United States Patent [19]
Hergenroeder

[11] Patent Number: 4,729,404
[45] **Date of Patent: * Mar. 8, 1988**

[54] RECEPTACLE FOR COLLECTING FLUID

[76] Inventor: Patrick T. Hergenroeder, 48 W. Orange St., Chagrin Falls, Ohio 44022

[ * ] Notice: The portion of the term of this patent subsequent to Jul. 14, 2004 has been disclaimed.

[21] Appl. No.: 23,201

[22] Filed: Mar. 9, 1987

Related U.S. Application Data

[63] Continuation of Ser. No. 869,441, May 27, 1986, Pat. No. 4,679,590, which is a continuation of Ser. No. 645,864, Aug. 31, 1984, abandoned.

[51] Int. Cl.[4] .............. A61M 1/00
[52] U.S. Cl. .............. 137/602; 137/561 R; 137/312; 137/362; 604/356
[58] Field of Search .............. 137/561 A, 561 R, 602, 137/362, 312; 604/317, 322, 356; 296/1 F; 269/327; 4/640; 222/108

[56] References Cited

U.S. PATENT DOCUMENTS

| | | | |
|---|---|---|---|
| 1,948,327 | 2/1934 | Berwick | 296/1 F |
| 2,546,394 | 8/1947 | Harmon | 296/1 F |
| 2,599,049 | 7/1947 | Dollinger | 15/301 |
| 2,650,855 | 6/1948 | Peirce | 296/1 F |
| 2,733,684 | 8/1953 | Trenchard | 119/28 |
| 3,032,062 | 5/1962 | Blahnik | 137/362 X |
| 3,082,032 | 6/1958 | Stata | 296/1 F |
| 3,699,926 | 10/1972 | Stockl | 119/28 |
| 4,243,214 | 1/1981 | LaRooka | 269/327 |
| 4,280,729 | 7/1981 | Morawski | 296/1 F |
| 4,369,532 | 1/1983 | Houchins et al. | 4/640 X |
| 4,420,180 | 12/1983 | Dupont et al. | 296/1 F |
| 4,537,217 | 8/1985 | Allen, Jr. | 137/561 A |

FOREIGN PATENT DOCUMENTS

| | | | |
|---|---|---|---|
| 698825 | 12/1964 | Canada | 296/1 F |

*Primary Examiner*—Alan Cohan
*Assistant Examiner*—John Rivell
*Attorney, Agent, or Firm*—Watts, Hoffmann Fisher & Heinke

[57] ABSTRACT

A receptacle 10 for collecting fluid, especially suitable for use on the floor of an operating room for collecting irrigating fluid during a surgical procedure, for example, during arthroscopic surgery on a joint, such as the knee. The receptacle is thin and generally flat, with a gridwork of small basins 12 that form a collecting surface 14 with drains 24 through which the fluid flows to channels 16 formed between the receptacle and floor and thence to a common discharge port 20, which suitably may be connected to a suction device, such as an aspirator.

5 Claims, 6 Drawing Figures

RECEPTACLE FOR COLLECTING FLUID

RELATED APPLICATIONS

This application is a continuation of U.S. Ser. No. 869,441, filed May 27, 1986, now U.S. Pat. No. 4,679,590, which is a continuation of U.S. Ser. No. 645,864 filed Aug. 31, 1984, now abandoned.

Technical Field

This invention relates to a receptacle for collecting fluid and more particularly to a receptacle in the nature of a mat for use on the floor of an operating room.

BACKGROUND ART

In certain arthroscopic surgical procedures saline solution is introduced about the area being operated on and circulation of such fluid is continued during the procedure. For example, in performing arthroscopic surgery on a knee joint, saline solution is forced under pressure into the knee joint through a tube inserted through a small incision in the overlying skin and synovial membrane and is removed through a second incision. Solution tends to escape during this process and typically runs onto the operating room floor, notwithstanding attempts to collect the flow by using plastic sheets draped in appropriate ways. Several gallons of fluid may be lost during a procedure that takes 45 minutes to an hour. In many instances use of the operating room is delayed between patients while solution that has accumulated on the operating room floor is removed.

DISCLOSURE OF INVENTION

The present invention provides a receptacle in the general form, i.e., size and shape, of a mat for support on a floor, constructed to effectively collect fluid that would otherwise fall onto the floor and to facilitate continual removal of the collected fluid. The receptacle is large enough to directly receive and collect fluid beneath a substantial area, such as the entire area where a saline solution may be escaping in a surgical procedure. The receptacle isolates collected fluid beneath an upper surface to avoid spillage or immersion of objects in the collected fluid, provides channels between the receptacle and the supporting floor for carrying away collected fluid, and facilitates movement of equipment on rollers across the receptacle when necessary.

The receptacle is molded of natural or synthetic rubber or suitable plastic, is flexible enough to conform to the general contour of the supporting surface, which is typically flat but may not be perfectly planar, has a tendency to cling to the supporting surface, and is relatively thin compared to its length and width. A lower surface forms seals with the support surface about the periphery of the receptacle and also along collecting channels in the lower surface. An upper surface forms a gridwork of shallow fluid-collecting basins, each with a drain that communicates to the lower surface and the collecting channels. The channels communicate with a manifold and a discharge port through which collected fluid is evacuated. This construction is economical to manufacture, effectively collects and contains fluid to permit its continual and convenient removal, is especially adapted for use directly on the floor of an operating room without obstructing passage of people or equipment, and eliminates the need for make-shift drapings and aprons to confine or collect fluid that would otherwise fall to the floor and require clean-up.

From the foregoing it can be appreciated that, in its broad form, the receptacle of the present invention is comprised of a thin body having a plurality of shallow basins in an upper surface and channels in a lower surface communicating with the basins, and a discharge port communicating with the channels. Those and other more specific features of the invention will become better understood from the detailed description that follows.

BEST MODE FOR CARRYING OUT THE INVENTION

Figure 3:
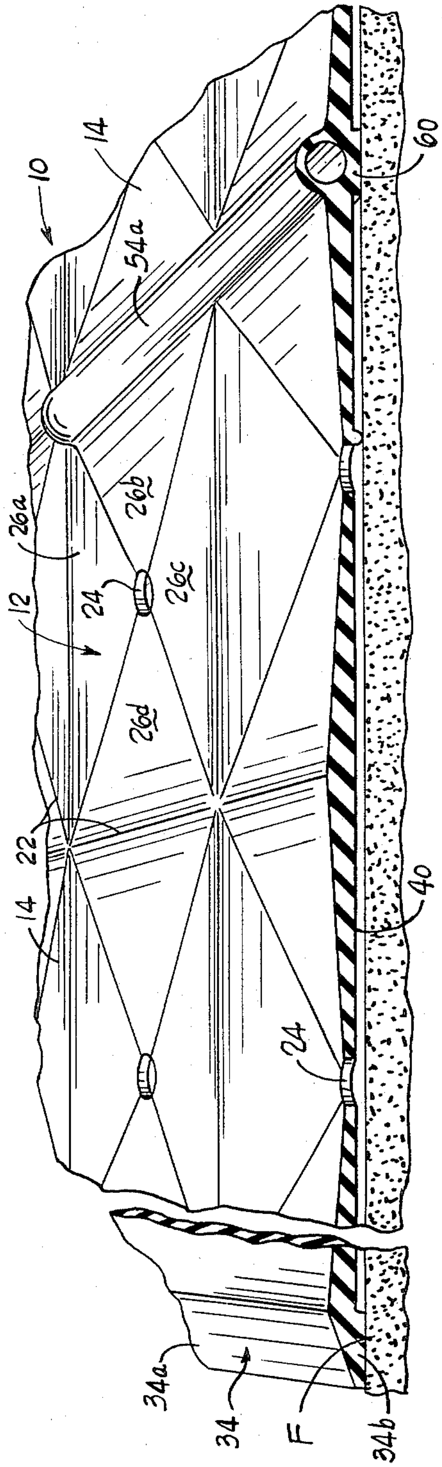
FIG. 3 is a fragmentary perspective view of the receptacle of FIG. 1, with parts broken away and parts in section.
Figure 5:
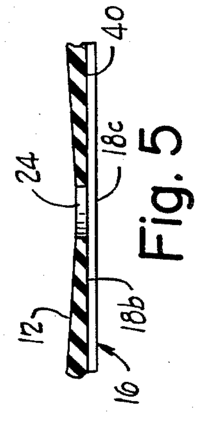
FIG. 5 is a partial sectional view of the embodiment of FIG. 1 taken along the line 5—5 of FIG. 1.
Figure 4:
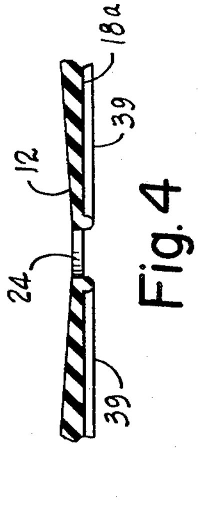
FIG. 4 is a partial sectional view of the receptacle of FIG. 1 taken along the line 4—4 of FIG. 1.
Figure 6:
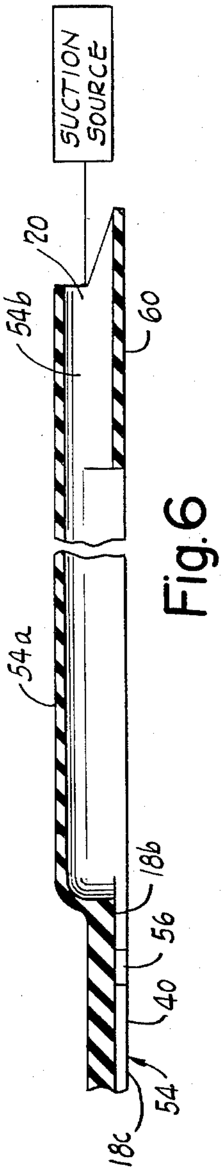
FIG. 6 is a partial sectional view taken along the line 6—6 of FIG. 1.

With reference to the drawings, a receptacle 10 is shown embodying the invention. In the preferred construction shown, the receptacle is of rectangular shape, thin relative to its length and width, and is generally flat in its extent, but has plural shallow basins 12 in a top surface 14, and recesses in the form of channels indicated generally by the reference numeral 16 in a bottom or base surface 18. The basins 12 drain into the channels 16. The receptacle 10 is adapted to rest on a floor F (FIG. 3) and forms a seal with the floor about the periphery of the receptacle and along the channels in the bottom surface. Fluid collected in the basins 12 and the channels 16 is removed through a discharge charge port 20, typically connected to a suction source (not shown).

In the preferred construction shown, the basins 12 are peripherally square and directly abut one another to form an array of adjacent basins. Each basin slopes from the four sides 22 that form the perimeter, centrally to a drain 24 in the form of a circular opening in the center of each basin. The sloping basin surface 26 is comprised of four flat triangular-shaped segments *26a–d*, the base of each triangular-shaped segment lying along a side 22 and the apex located at the drain. The circular opening forming the drain 24 extends through the receptacle 10, communicating from the top surface 14 to the bottom surface 18.

The sides 22 of the basins 12 form a gridwork of ridges 27 that run both parallel and perpendicular to side edges 28, 29, 30, 31 of the receptacle. The ridges formed by the junctures of the adjacent basins are essentially lines without flat surface areas between basins. As a result, there is no portion of the top surface 14 of the receptacle where standing fluid can accumulate; rather, all areas within the side edges 28–31 direct any fluid received toward the drains 24. Also, by virtue of the many basins 12, which are small relative to the overall receptacle size, the slope of the segments *26a–d* is sufficiently steep, notwithstanding the small height of the receptacle, to promote rapid flow of fluid along the segment surfaces to the drains.

A peripheral tapered lip 34 surrounds the array of basins 12 directly adjacent the side edges 28–31. An inclined upper surface 34*a* minimizes the obstructive effect of the receptacle when positioned on the floor of a room. A lower surface 34*b* is flat and adapted to lie against the supporting floor and form a peripheral seal with the floor about the receptacle 10.

The bottom surface 18 of the receptacle 10 includes a grillwork of ridges or walls 38 (FIG. 2) that follow the perimeters of the basins 12, i.e., that underly the sides 22 of each basin and extend from recessed bottom surface portions 18*a* between the walls. The bottom surface also includes diagonal walls 39 that extend from the corners formed by the walls 38 toward the drains 24, terminating at the perimeter of each drain. The walls 38 and 39 serve to support the receptacle 10 on the floor F and reduce the thickness of the material that forms the basins 12, thereby reducing the weight of the receptacle 10 and the material cost.

Figure 1:
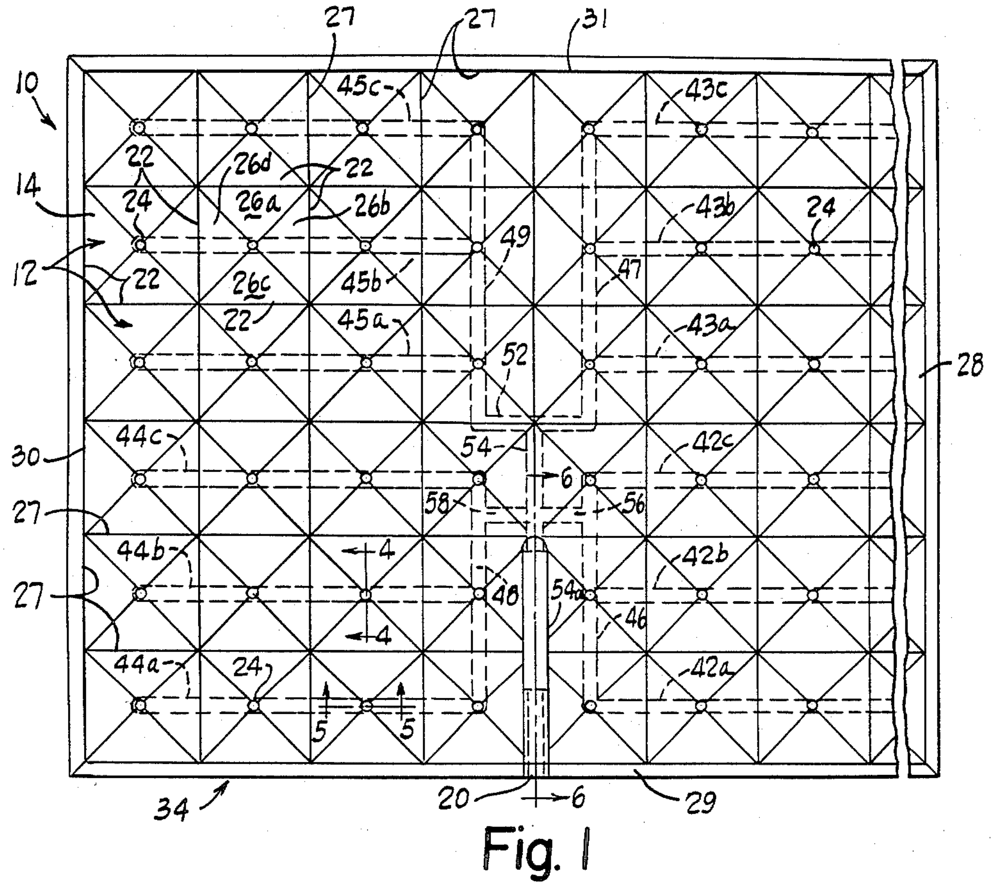
FIG. 1 a top plan view of a receptacle embodying the present invention.
Figure 2:
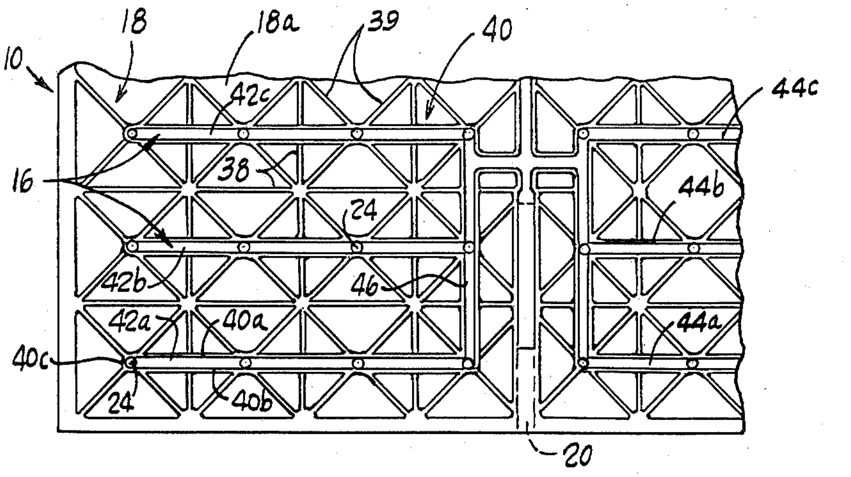
FIG. 2 is a partial bottom view of the receptacle of FIG. 1.

Additional ridges or walls 40 formed in the bottom surface 18, of equal height to the walls 38 and 39, and with recessed surface portions 18*b* between them, extend in parallel pairs to form the various recesses in the form of the channels 16 in the bottom surface 18. Several pairs of such walls form specific collecting channels 42 beneath a number of aligned drains 24. Each wall 40 of the pairs forming the collecting channels 42 is spaced from the other a distance equal to the diameter of the drains. As best shown in FIG. 2, two such walls designated 40*a*, 40*b* and a connecting cross wall 40*c* at one end form a collecting channel 42*a* beneath four aligned drains 24. The channel 42*a* terminates at the end opposite from the cross wall 40*c* in communication with a specific header channel 46 of the various channels 16. Two other collecting channels 42*b*, 42*c*, formed by other walls 40, connect with the header channel 46 and each one underlies the drains 24 of four basins 12. Three additional collecting channels 43*a*, *b*, *c*, as shown in phantom in FIG. 1, similarly formed by walls 40, underly three rows of aligned drains 24 and terminate in a header channel 47; three additional collecting channels 44*a*, *b*, *c* each underly three other rows of aligned drains and terminate in a header channel 48; and three collecting channels 45*a*, *b*, *c* each underly another three rows of aligned drains an connect to a header channel 49. Each header channel 46–49 is formed of parallel walls 40 that in part form the bottom surface 18 of the receptacle.

The two header channels 47, 49 are connected by a feeder channel 52, in turn communicating with a discharge channel 54. The header channel 46 has a feeder channel 56 communicating with the discharge channel 54, and the header channel 48 has a feeder channel 58 communicating with the discharge channel 54. The feeder and discharge channels are formed of walls 40, except that a portion 54*a* of the discharge channel 54 is raised above the level of the basins, and a terminal portion 54*b* is tubular by virtue of a bottom wall 60. The discharge channel portion 54*b* terminates in the discharge port 20 at the edge 29 of the receptacle. The tubular portion 54*b* is adapted to receive a nipple or fitting to connect a tube from an aspirator or other suction device that removes fluid from the discharge channel 54 and associated feeder, header and collecting channels.

The walls 40 forming the collecting, header, feeder and discharge channels provide suitable depth to the channels sufficient to allow receipt of fluid through the drains 24 and sufficient to accommodate flow of fluid beneath the recessed bottom surface portions 18*b* that form the tops of the various channels, between the channel-forming walls. In the preferred embodiment, the recessed bottom surface 18*b* between the channel-forming walls is at the same level above bottom surface portions 18*c* of the walls 40 as is the recessed surface portions 18*a*. The wall bottoms 18*c* form seals with the supporting floor F to effectively confine the collected fluid to the collecting, header, feeder and discharge channels. However, in the event any leakage from the channels should occur, the leakage will be received in the areas or zones between the walls 38, 39 underlying the basins, and ultimately will be confined by the bottom surface 34*b* of the tapered lip 34.

It will be understood that the entire bottom surface 18 could be flat, with only the various channels formed therein as grooves, but without the savings in weight and material gained with the preferred embodiment.

In use, the receptacle 10 is placed on a floor F, where falling fluid is to be collected. Fluid dropping onto the top surface 14 of the receptacle will be caught in one or more of the basins 12, flow down the triangular shaped surfaces 26 to the center of the basin or basins, and through the central drains 24. The appropriate underlying collecting channels 42, 43, 44, 45 will conduct the fluid received from the drains to the connected header channel 46, 47, 48, 49 and thence to the connected feeder channel 52, 56, 58 and to the discharge channel 54, to which suction is applied, removing the fluid through the discharge port 20. Thus, fluid collected is immediately removed from the top surface 14 to a location beneath the receptacle, between the receptacle and floor F, where it is isolated against spilling and whereby splashing is minimized as additional fluid is collected. The arrangement facilitates the continual removal of collected fluid so that large quantities of fluid can be collected, notwithstanding the relatively small height and volume of the receptacle.

The seal formed between the bottom surface of the receptacle and the floor prevents leakage, and in addition, use of the floor to in part form the collection and discharge conduits keeps the height of the receptacle to a minimum. The material of which the receptacle is formed is flexible and sufficiently soft to achieve a good seal with a smooth floor typical of surgical operating rooms. Where the area for fluid collection is large, several mats can be arranged next to one another to form a solid area of receptacles for collecting fluid over the larger area.

By way of example only and not by way of limitation, a preferred embodiment of the invention, found especially suitable for use in surgical operating rooms for arthroscopy, particularly arthroscopy of the knee joint, utilizes a receptacle as shown in the drawings, having dimensions of 33 inches×25 inches in length and width, respectively, and $\frac{1}{4}$ inch in height (except for the portion 54*a* and 54*b* of the discharge channel, which is approximately $\frac{1}{2}$ inch in height. Each of the basins 12 is 4 inches square. The lip 34 is $\frac{1}{2}$ inch in width, $\frac{1}{4}$ inch in height at its inward edge and approximately 0.06 inch in height at its outer edge. Each drain opening is 0.31 inch in diameter. The height of the walls 40 that form the collecting, header and feeder channels, as well as the walls 38, 39, are 0.06 inch in height, providing channels of that same depth in the bottom surface 18. The discharge port 62 is 0.312 inch in diameter. The preferred embodiment is molded of a blend of vulcanized natural and/or synthetic elastomers.

While a preferred embodiment of the invention has been described in detail, it will be apparent that modifications and alterations may be made therein without departing from the spirit and scope of the invention set forth in the appended claims.

I claim:

1. A receptacle adapted for continuous and simultaneous collection and disposal of impinging fluid, said receptacle comprised of a body of small thickness relative to its length and width and having a lower surface comprising fluid containment means for containing fluid beneath the lower surface and further having an upper surface comprising fluid collection means for collecting fluid on the upper surface, said upper surface in fluid-flow communication with said lower surface, and said lower surface in fluid-flow communication with a discharge port adapted to connect with a suction source for disposal of the fluid.

2. A receptacle as claimed in claim 1 wherein said fluid containment means comprises a cavity beneath the lower surface and a lower edge of the receptacle about the cavity that engages and substantially seals against a receptacle-supporting surface.

3. A receptacle as claimed in claim 1 wherein said fluid collection means comprises an upper peripheral edge of the receptacle.

4. A receptacle as claimed in claim 1 wherein said fluid collection means comprises a shallow basin formed by said upper surface, said basin having a drain that communicates to said lower surface.

5. A receptacle as claimed in claim 1 wherein said fluid containment means comprises channels formed by the lower surface in fluid-flow communication with the upper surface and with said discharge port, said channels having edges that seal against a receptacle-supportive surface.

* * * * *